United States Patent [19]

Weber

[11] Patent Number: 5,783,743
[45] Date of Patent: Jul. 21, 1998

[54] MOISTURE SENSOR

[75] Inventor: Klaus Weber, Kronberg, Germany

[73] Assignee: VDO Adolf Schindling AG, Frankfurt, Germany

[21] Appl. No.: 671,136

[22] Filed: Jun. 27, 1996

[30] Foreign Application Priority Data

Jul. 8, 1995 [DE] Germany .......... 195 24 942.9
Jan. 24, 1996 [DE] Germany .......... 196 02 354.8

[51] Int. Cl.⁶ .......... H01G 5/20; G01N 27/12; H02P 1/04; G01R 27/26
[52] U.S. Cl. .......... 73/29.01; 324/664; 324/71.1; 324/694; 29/610.1; 29/620; 29/851; 73/335.05; 340/602
[58] Field of Search .......... 73/29.01, 335.05; 324/664, 694, 71.1; 340/602, 604; 29/620, 851, 860, 610.1, 611

[56] References Cited

U.S. PATENT DOCUMENTS

| | | | |
|---|---|---|---|
| 2,993,815 | 7/1961 | Treptow | 117/212 |
| 3,647,532 | 3/1972 | Friedman et al. | 117/212 |
| 3,748,625 | 7/1973 | Bennewitz | 338/34 |
| 3,906,426 | 9/1975 | Frazee et al. | 338/35 |
| 3,983,527 | 9/1976 | Ohsata et al. | 338/35 |
| 4,050,048 | 9/1977 | Frazee | 338/35 |
| 4,072,771 | 2/1978 | Grier, Sr. | 427/96 |
| 4,163,384 | 8/1979 | Blakemore | 73/29 |
| 4,172,922 | 10/1979 | Merz et al. | 428/432 |
| 4,326,404 | 4/1982 | Mehta | 73/29 |
| 4,540,604 | 9/1985 | Siuta | 427/96 |
| 4,554,493 | 11/1985 | Armstrong | 318/444 |
| 4,639,831 | 1/1987 | Iyoda | 361/286 |
| 4,642,887 | 2/1987 | Fredriksson | 29/611 |
| 4,644,139 | 2/1987 | Harrison et al. | 219/522 |
| 4,737,629 | 4/1988 | Iwama et al. | 250/231 R |
| 4,805,070 | 2/1989 | Koontz et al. | 361/286 |
| 4,815,198 | 3/1989 | Ramus | 29/611 |
| 4,827,198 | 5/1989 | Mueller et al. | 318/483 |
| 4,831,493 | 5/1989 | Wilson et al. | 316/286 |
| 4,870,746 | 10/1989 | Klaser | 29/620 |
| 4,919,744 | 4/1990 | Newmann | 156/308 |
| 5,039,840 | 8/1991 | Boardman | 219/270 |
| 5,040,411 | 8/1991 | Medzius | 73/73 |
| 5,048,336 | 9/1991 | Sugihara et al. | 73/336.5 |
| 5,054,190 | 10/1991 | Inoue et al. | 29/611 |
| 5,319,975 | 6/1994 | Pederson et al. | 73/335.01 |
| 5,323,637 | 6/1994 | Bendicks et al. | 73/29.01 |
| 5,467,522 | 11/1995 | Gold | 29/611 |
| 5,598,146 | 1/1997 | Schröder | 340/602 |

*Primary Examiner*—Hezron E. Williams
*Assistant Examiner*—J. David Wiggins
*Attorney, Agent, or Firm*—Martin A. Farber

[57] ABSTRACT

A sensor for detecting moisture on a non-conductive support, in particular a windshield of a motor vehicle, has one or more metallic, electrically conductive layers which are arranged in a given pattern on the outer surface of the support. The metallic, electrically conductive layer is produced from a metallic resinate which is applied to the support and then burned-in by the action of heat. Also described is a method for constructing such a moisture sensor whit applies a glass layer in the form of a glass frit paste to be sintered upon the metallic electrically conductive layer, where the burning-in of the metallic resinate and the sintering of the glass frit paste are effected in single step.

40 Claims, 3 Drawing Sheets

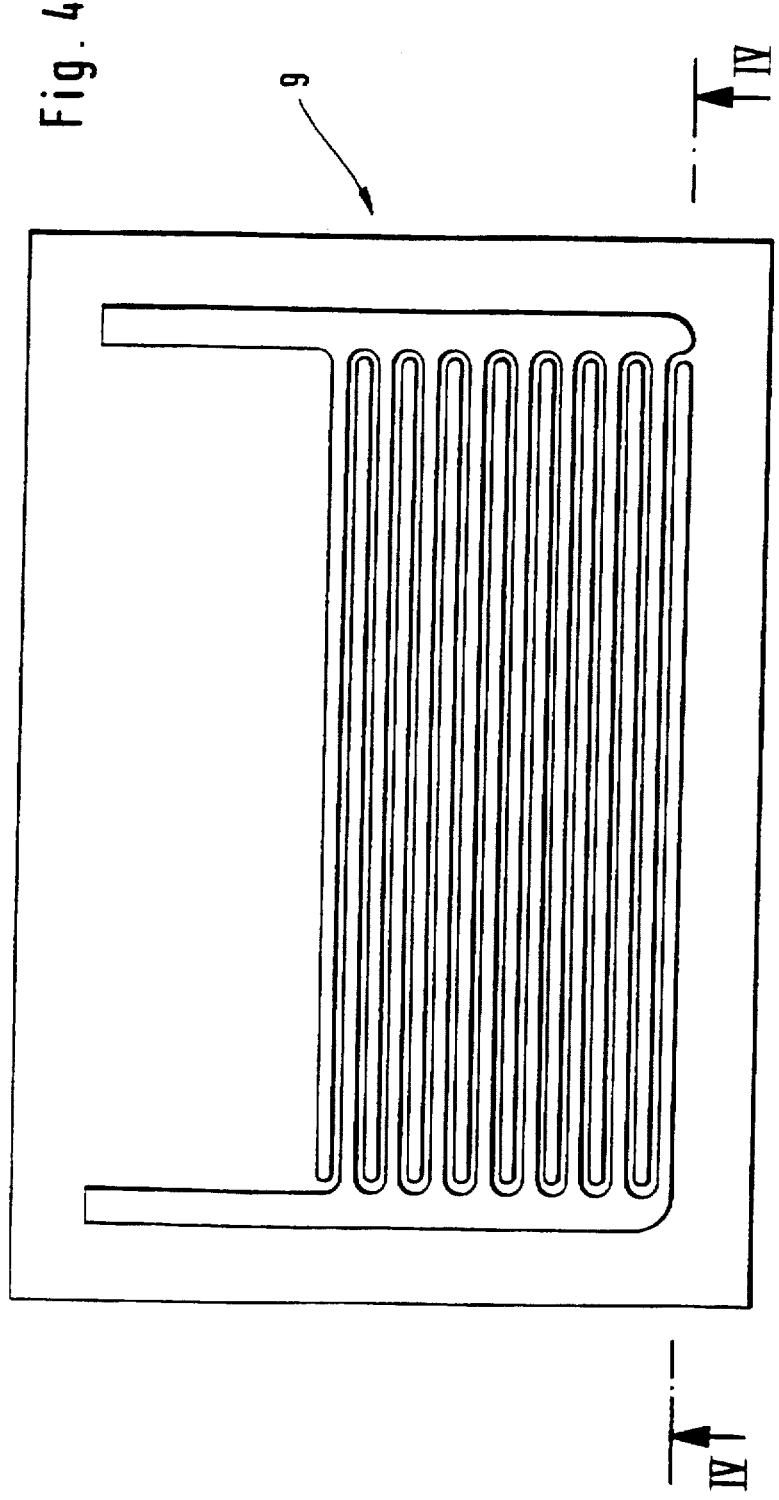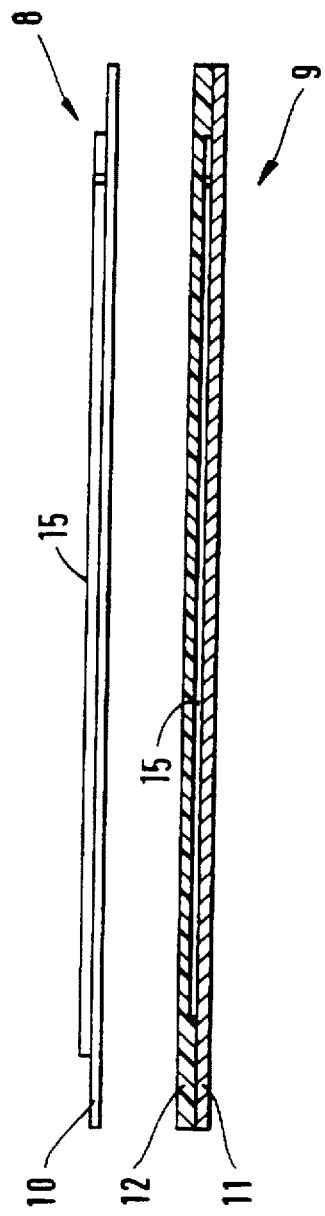

MOISTURE SENSOR

FIELD AND BACKGROUND OF THE INVENTION

The present invention relates to a sensor for detecting moisture on a non-conductive support, in particular the windshield of a motor vehicle, the sensor having one or more metallic electrically conductive layers which are arranged in a given pattern on the outer surface of the support.

Metallic, electrically conductive layers on vehicle windows serve, for instance, to form a resistive rain sensor. However, they may also be used for the electrical heating of the window or to form an antenna for a radio. Such conductive paths should adhere firmly as well as possible to the window, so that they cannot loosen from the window when it is cleaned, or as a result of environmental influences. This applies, in particular, to conductive paths which serve as rain sensors since rain sensors must lie within the field of action of the windshield wiper and, during the cleaning, the windshield wiper moves continuously over these conductive paths. Aside from good adherence to the window of the vehicle, such conductive paths should also, therefore, be as resistant to abrasion as possible. The maintaining of precise dimensions of the conductive paths is also frequently necessary.

In order to satisfy these requirements, conductive paths have been applied up to now to vehicle windows by vapor deposition. Vapor deposition methods are, however, very expensive and lead to undesirably strong differences in dimensions, so that sufficiently reproducible sensor signals cannot be obtained with a sensor formed by such conductive paths.

SUMMARY OF THE INVENTION

It is an object of the invention to provide a sensor of the aforementioned type which adheres firmly to the supporting glass.

According to the invention, a metallic electrically conductive layer is produced from a metallic resinate which is applied to the vehicle window and then burned-in by the action of heat. By the burning-in of the metallic resinate, the resinate is converted into a conductive metal, the latter adhering very strongly to the supporting glass.

The electrically conductive layer may preferably consist of platinum, gold, silver, or palladium.

The sensor can be produced in simple manner by mixing resinate particles in a printing-support composition so as to form a conductive paste, and applying the paste by screen printing onto the supporting window.

The thickness of the electric layer can be kept very small when a resinate is used, and the layer preferably has a thickness of about <0.5 µm. Thus, the layer is in no way impaired when, for instance, a windshield wiper blade wipes over the layer.

The support is preferably a pane of glass.

In order to protect the metallically conductive layer from abrasion, it can be covered by a protective layer.

Such a protective layer can be a galvanically applied, electrically conductive layer, in which case, in the event of an electrically conductive layer of gold, the galvanically applied layer preferably consists of rhodium.

In another embodiment, the protective layer can be an electrically insulating layer having, at a slight distance from each other, a plurality of recesses (6) which leave the conductive layer free. Due to the recesses, assurance is had that a conductive connection between adjacent electrically conductive layers can be produced by moisture.

The protective layer may be a layer of glass. This layer of glass may be produced in simple manner if the layer of glass is a layer printed as a glass frit paste and sintered by the action of heat. The glass frit paste is possibly applied to the electrically conductive layer by screen printing.

The process is also simplified if the burning-in of the metallic resinate and the sintering of the glass-frit paste are effected in a single heating step.

The electrically conductive layer is preferably a resistance layer (1, 1'). The sensor can have a pattern with at least two path-shaped conductive layers which extend at a slight distance from each other. The path-shaped conductive layers which extend alongside of each other are adapted to be connected to different electrical potentials.

If the ends of the path-shaped conductive layers are conducted around a side edge (4) of the pane of glass onto the inner surface of the pane, then the connection to the electric potential can be made inside the motor vehicle without expensive wiring.

The sensor is preferably a resistive rain sensor, the resistance between two path-shaped conductive layers being dependent on the amount of moisture covering both of the two layers.

If a conductive path of high electrical conductivity is arranged on the support between the support and the resistance layer, then the resistance to be detected is dependent substantially only on the amount of moisture covering the sensor and less on its specific conductivity.

The sensor of the invention can be produced in simple fashion wherein the metallic resinate is applied in the given pattern on a flexible foil (10) and dried. Thereupon a flexible-foil (10) is applied to the outer surface of the pane of glass, and the pane of glass, together with the foil, is subjected to the action of heat in order to burn off the foil and sinter the resinate on the support and form the metallic, electrically conductive layer. This not only makes it possible to produce the sensor pattern independently of the pane of glass, which is generally of large size, and only then apply it on the glass, but, in addition, also to effect a simple application on curved glass in view of the flexibility of the foil.

These advantages are present also in another process for the manufacture of the sensor in which the metallic resinate is applied in the given pattern onto a support sheet (11) and dried. A side of the support sheet (11) bearing the resinate is covered by a flexible foil layer (12). Adherence of the foil to the resinate pattern is greater than adherence of the support sheet (11) to the resinate pattern. This enables separation of the support sheet from the foil layer (12) bearing the resinate pattern. The foil layer is applied to the outer surface of the pane of glass, and the pane of glass bearing the foil layer (12) is acted on by heat in order to burn off the foil layer (12) and sinter the resinate onto the pane of glass as well as form the metallic, electrically conductive layer. The use of a support sheet, which can be a sheet of paper, permits particular protection of the sensor pattern while it is still separate from the pane of glass.

After the sintering-on of the resinate, the metallic electric conductive layer formed thereby can be provided with a protective layer by dipping,of the electric conductive layer into an electroplating bath.

Another aspect of the invention provides that, before the application of the resinate in the given pattern, a glass-frit paste is applied for the production of a protective layer (5) on the flexible foil (10). Also the metallic resinate is then applied on the glass-frit paste pattern. Alternately, before the application of the foil layer on the resinate pattern, in order to produce the protective layer a glass frit paste is applied on the resinate pattern.

The foil (10) or foil layer (12) is preferably a plastic film which is vaporized without a leaving of residue during the sintering process.

The sintering can be effected at a temperature which corresponds approximately to the deformation temperature for the plastic deformation of the pane of glass, the sintering being effected at a temperature of between about 500° C. and 700° C., and preferably at a temperature of about 600° C.

If the resinate is applied to the flat pane of glass and sintered on it with simultaneous deformation by bending-of the pane of glass, then the sintering and the shaping of the pane of glass are effected in a single operation. The deformation by bending can be effected both by gravitational bending and by press bending in a press-bending furnace.

In-order to improve the resistance to scratching of the resinate, after the deformation by bending, a region of the pane of glass bearing the resinate is heated for a short time at a temperature which is above the deformation temperature for the plastic deformation of the pane of glass. The additional-heating is effected in this connection at a temperature of more than 700° C. The additional heating is limited to a period of time of at most 30 seconds.

A sensor arrangement for the carrying out of the process described can, in one embodiment, be developed in the manner that the intended pattern consisting of a sinterable resinate is applied to a flexible sheet or foil (10). The flexible sheet (10) is vaporizable at a temperature corresponding approximately to the sintering temperature of the resinate.

In a further embodiment, the intended pattern of a sinterable resinate is applied on a support sheet (11). Then a flexible foil layer (12) is applied on the support sheet (12) covering the intended resinate pattern. The adherence of the resinate pattern to the support sheet (11) is less than to the foil layer (12), and the flexible foil layer (12) is vaporizable at a temperature corresponding approximately to the sintering temperature of the resinate.

BRIEF DESCRIPTION OF THE DRAWINGS

With the above and other objects and advantages in view, the present invention will become more clearly understood in connection with the detailed description of preferred embodiments, when considered with the accompanying drawings, of which: FIG. 4 is a top view of an alternative embodiment of the sensor; FIG. 5 is a cross section through the sensor of FIG. 4 along the line IV—IV; and FIG. 6 is a side view of another embodiment of a sensor.

DETAILED DESCRIPTION OF THE PREFERRED EMBODIMENT

Figure 1:
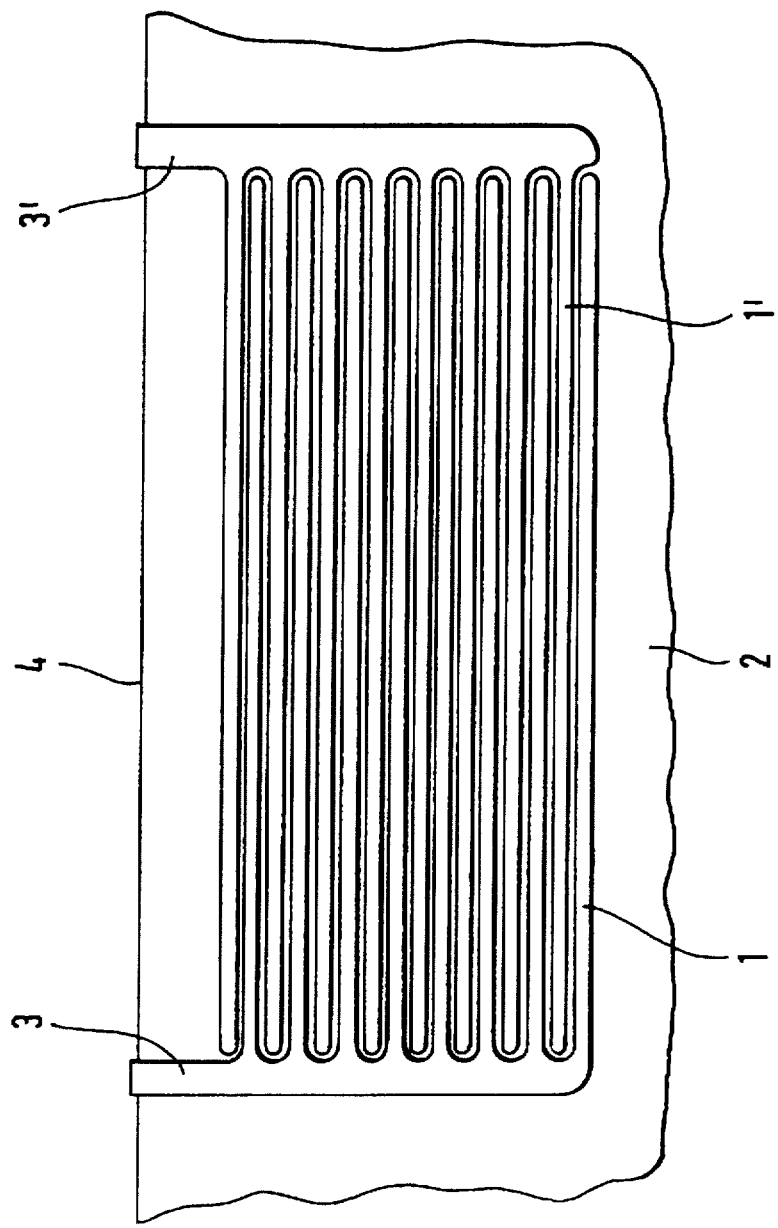
FIG. 1 is a top view of a sensor.

The rain sensor shown in FIG. 1 consists of two electrically conductive resistance layers 1 and 1' applied to the outer surface of a windshield 2, the resistance layers being developed in comb-like manner with the teeth of their combs engaging into each other so that only slits of slight width are present between the teeth. The resistance layers 1 and 1' have connection contacts 3 and 3' respectively which extend around the side edge 4 of the windshield 2 onto the inner surface of the windshield 2 and can be connected to different electric potentials. Drops of water which strike the windshield 2 and bridge over the slits, establish a conductive connection between the teeth, the detectable resistance of which connection depends on the quantity of water drops bridging over the slits.

The teeth of the resistance layers 1 and 1' may have a width on the order of magnitude of 100 μm, and the slits between the teeth may have a width on the order of magnitude of 400 μm.

Figure 2:
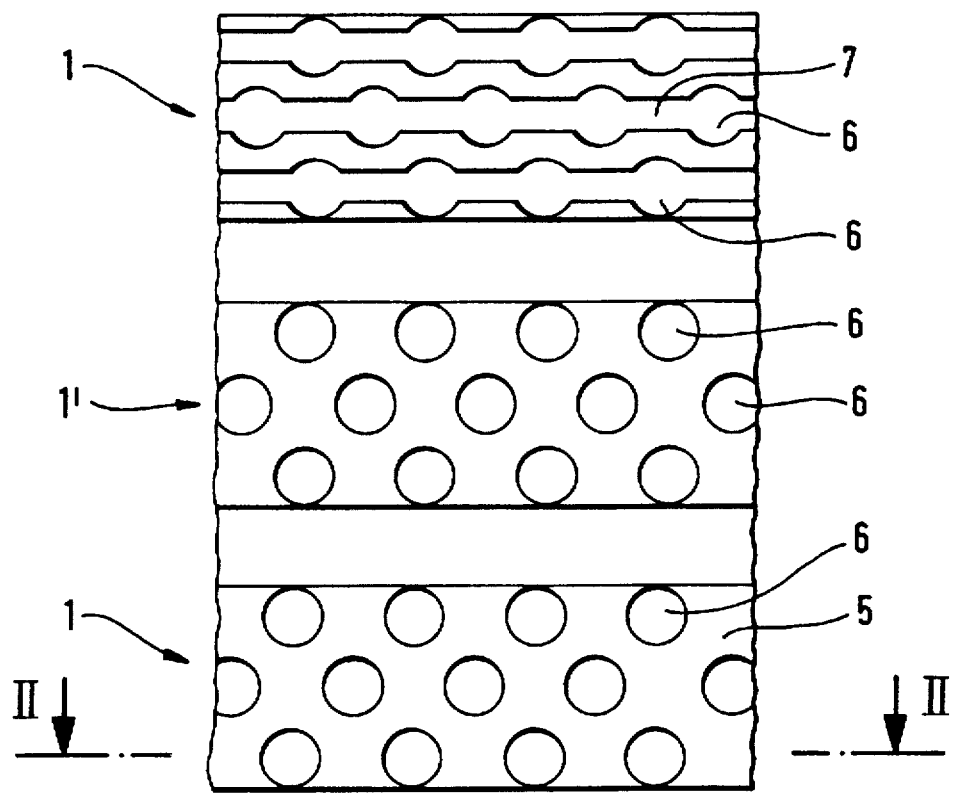
FIG. 2 is an enlarged portion of a top view of three electrically conductive layers of a sensor in accordance with FIG. 1.
Figure 3:
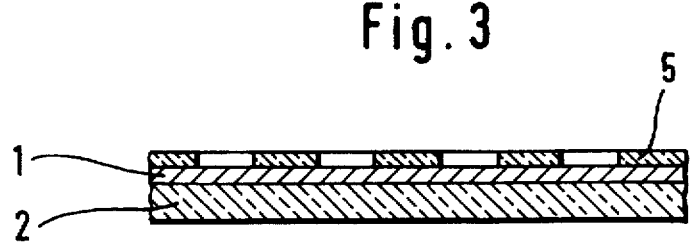
FIG. 3 is a cross section through the sensor of FIG. 2 along the line II—II.

As can be noted from FIGS. 2 and 3, the resistance layers 1 and 1' are covered by a protective layer 5 of glass which has a plurality of closely adjacent recesses 6 which extend through it and leave the resistance layers 1 and 1' free in their region. As shown in the case of the top resistance layer 1, these recesses can be connected, in addition, to each other by continuous slits 7. By these recesses 6 and possibly slits 7, a conductive connection can be produced between the resistance layers 1 and 1' by drops of water impinging on the resistance layers.

FIGS. 4 to 6 show sensor arrangements 8 and 9 of two alternately applied preferred embodiments which are produced separately from the windshield 2 and then applied onto the windshield 2.

In the embodiment of the sensor arrangement 8 shown in FIG. 6, a resinate 15 is applied onto a flexible foil 10 of a plastic by screen printing in the pattern of the resistance layers 1 and 1' and dried. This prefabricated sensor arrangement can now be so placed on a preferably flat windshield 2 that its connection contacts 3 and 3' protrude beyond the side edge 4 (FIG. 1) of the windshield 2 and are folded around the edge 4 and against the rear of the windshield 2. Since the foil 10 is adherent to the glass windshield 2, the foil 10 remains in the position in which it has been applied on the windshield 2.

By the action of heat on the windshield 2, in a bending furnace with a temperature of about 600° C., the resinate 15 is sintered onto the windshield 2, the flexible foil 10 is completely vaporized, and a deformation by bending of the windshield 2 out of its flat shape into a curved shape take place simultaneously.

After the deformation by bending of the windshield 2, the layer of glass which bears the resinate 15 is heated for about 15 seconds to a temperature of about 700° C. This is most easily done by an additional heating which is so arranged in the bending furnace that it is directly opposite the sensor arrangement 8 in the immediate vicinity thereof. This additional heating is then turned on for the above-indicated period of time after the conclusion of the deformation-by bending..

Upon the application of the foil onto the windshield 2, this can be done both with the side bearing the resinate 15 as well as with the side of the foil 10 facing away from the resinate 15 .

In the embodiment of the sensor arrangement 9 shown in FIGS. 4 and 5, a resinate 15 is applied onto a support sheet 11 of for instance paper in the pattern of the resistance layers 1 and 1' and dried in a drying furnace. The resinate pattern is then covered over its entire surface with a plastic paste which, upon drying, forms a flexible foil layer 12.

In the case of this previously prepared sensor arrangement 9, the support sheet 11 can now be removed in accordance with the principle of a decalcomania and the flexible foil applied, in the same way as the foil 10 in the embodiment of FIG. 6, to the windshield 2 and sintered thereon.

Since the adherence of the resinate 15 to the support sheet is substantially less than its adherence to the flexible foil layer 12, the resinate pattern always remains on the foil layer 12 upon the separation of support sheet 11 and flexible foil layer 12.

As a result of the support sheet 11, the sensor arrangement 9 is very practical to handle since there is no danger of the unintended adhering of the flexible foil sheet 12 before the pulling-off of the support sheet 11 that must precede the sintering of the foil sheet 12.

I claim:

1. A sensor for detecting moisture on a non-conductive support, suitable for the windshield of a motor vehicle, the sensor having as an eletrode one or more metallic electrically conductive layers which are arranged as teeth in a given pattern on the outer surface of the support without a conductive intermediate layer therebetween, the sensor detecting the moisture by an electrical impedance change resulting from one or more droplets bridging a plurality of the teeth;

wherein the metallic electrically conductive layer comprises a burned-in metallic resinate burned into the support by the action of heat.

2. A sensor according to claim 1, wherein the support is a vehicle window,' and the electrically conductive layer is made of platinum.

3. A sensor according to claim 1, wherein the support is a vehicle window, and one of the electrically conductive layer is made of gold.

4. A sensor according to claim 1, wherein the support is a vehicle window, and the electrically conductive layer is made of palladium.

5. A sensor according to claim 1, wherein the metallic resinate comprises resinate particles of a printing-support composition mixed so as to form a conductive paste suitable for screen printing onto the support, the support being a vehicle window.

6. A sensor for detecting moisture on a non-conductive support, including the windshield of a motor vehicle, the sensor having one or more metallic electrically conductive layers which are arranged in a given pattern on the outer surface of the support;

wherein the metallic electrically conductive layer comprises a metallic resinate disposed on the support and burned-in by the action of heat; and the thickness of the metallic electrically conductive layer is about <0.5 μm.

7. A sensor according to claim 1, wherein there is a plurality of said layers, and the support is a pane of glass.

8. A sensor according to claim 1, further comprising a protective layer covering the metallic electrically conductive layer to prevent abrasion.

9. A sensor for detecting moisture on a non-conductive support, including the windshield of a motor vehicle, the sensor having one or more metallic electrically conductive layers which are arranged in a given pattern on the outer surface of the support;

wherein the metallic electrically conductive layer comprises a metallic resinate disposed on the support and burned-in by the action of heat;

the sensor further comprises a protective layer covering the metallic electrically conductive layer to prevent abrasion; and the protective layer is a galvanically applied, electrically conductive layer.

10. A sensor according to claim 9, wherein, the galvanically applied layer is made of rhodium.

11. A sensor according to claim 8, wherein, the protective layer is an electrically insulating layer having a set of recesses arranged spatially apart, at a slight distance from each other, so as to form a plurality of recesses which leave the conductive layer exposed.

12. A sensor according to claim 11, wherein the protective layer is a layer of glass.

13. A sensor for detecting moisture on a non-conductive support, including the windshield of a motor vehicle, the sensor having one or more metallic electrically conductive layers which are arranged in a given pattern on the outer surface of the support;

wherein the metallic electrically conductive layer comprises a metallic resinate disposed on the support and burned-in by the action of heat;

the sensor comprises a protective layer covering the metallic electrically conductive layer to prevent abrasion;

the protective layer is an electrically insulating layer having a set of recesses arranged spatially apart, at a slight distance from each other, so as to form a plurality of recesses which leave the conductive layer exposed;

the protective layer is a layer of glass; and the layer of glass is a layer printed as a glass frit paste and sintered by the action of heat.

14. A sensor according to claim 13, wherein the glass frit paste is printable upon the electrically conductive layer by screen printing.

15. A method of constructing a sensor for detecting moisture on a non-conductive support, including the windshield of a motor vehicle, the sensor having one or more metallic electrically conductive layers which are arranged as teeth in a given pattern on the outer surface of the support;

wherein the metallic electrically conductive layer comprises a burned-in metallic resinate burned into the support by the action of heat;

the method comprising the steps of:

burning in the metallic resinate into said support;

applying a glass layer in the form of a glass frit paste by sintering said glass frit paste upon said metallic electrically conductive layer; and wherein the burning-in of the metallic resinate and the sintering of the glass-frit paste are effected in a single heating step.

16. A sensor according to claim 1, wherein an individual metallic electrically conductive layer is a chemically modified layer having significantly higher electrical resistance than any other of said one or more metallic electrically conductive layers.

17. A sensor according to claim 1, wherein the sensor has a pattern with at least two path-shaped conductive layers which extend at a slight distance from each other, the path-shaped conductive layers which extend alongside of each other being adapted to be connected to different electrical potentials.

18. A sensor for detecting moisture on a non-conductive support, including the windshield of a motor vehicle, the sensor having one or more metallic electrically conductive layers which are arranged in a given pattern on the outer surface of the support;

wherein the metallic electrically conductive layer comprises a metallic resinate disposed on the support and burned-in by the action of heat;

the sensor has a pattern with at least two path-shaped conductive layers which extend at a slight distance from each other, the path-shaped conductive layers which extend alongside of each other being adapted to be connected to different electrical potentials; and the support is a pane of glass, and the ends of the path-shaped conductive layers form leads that are conducted around a side edge of the pane of glass onto an inner surface of the pane.

19. A sensor according to claim 1, wherein the sensor is a resistive rain sensor, a resistance between two path-shaped conductive layers being dependent on the amount of moisture covering both of the two layers.

20. A sensor for detecting moisture on a non-conductive support, including the windshield of a motor vehicle, the sensor having one or more metallic electrically conductive layers which are arranged as teeth in a given pattern on the outer surface of the support without a conductive intermediate layer therebetween, the sensor detecting the moisture by an electrical impedance change resulting from one or more droplets bridging a plurality of the teeth;

wherein the metallic electrically conductive layer comprises a metallic resinate disposed on the support and burned-in by the action of heat; and the electrically conductive layer is a resistance layer, the sensor further comprising a conductive path of high electrical conductivity which is arranged on the support between the support and the resistance layer.

21. A method according to claim 15, wherein, prior to said burning step, there are steps of applying the metallic resinate in a given pattern on a flexible foil and drying the resinate, said support being a pane of glass;

applying the flexible foil to an outer surface of the pane glass; and wherein the burning step comprises a further step of heating the pane of glass, together with the foil, in order to burn off the foil and sinter the resinate on the support and form the metallic electrically conductive layer.

22. A method according to claim 15, wherein, prior to said burning step, there are steps of applying the metallic resinate in a given pattern onto a support sheet, and drying the resinate;

covering a side of the support sheet bearing the resinate by a flexible foil layer, the adherence of the foil layer to a pattern of the resinate being greater than the adherence of the support sheet to the resinate pattern;

separating the support sheet from the foil layer bearing the resinate pattern, said support being a pane of glass;

applying the foil layer to the outer surface of-the pane glass; and wherein, in said burning step, there is heating of the pane of glass bearing the foil layer in order to burn off the foil layer and sinter the resinate onto the pane of glass as well as to form the metallic, electrically conductive layer.

23. A method according to claim 21, wherein after the sintering-on of the resinate, there is a step of covering the metallic electric conductive layer with a protective layer by dipping the conductive layer into an electroplating bath.

24. A method according-to claim 22, wherein after the sintering-on of the resinate, there is a step of covering the metallic electric conductive layer with a protective layer by dipping the conductive layer into an electroplating bath.

25. A method according to claim 21, wherein, before the application of the resinate in the given pattern, there is a step of applying a glass-frit paste pattern for the production of a protective layer on the flexible foil, and a further step of applying the metallic resinate on the glass-frit paste pattern.

26. A method according to claim 22, wherein, before the application of the foil layer on the resinate pattern in order to produce the protective layer, there is a step of applying a glass frit paste on the resinate pattern.

27. A method according to claim 21, wherein the foil is a plastic film.

28. A method according to claim 22, wherein the foil is a plastic film.

29. A method according to claim 21, wherein the sintering is effected at a temperature which corresponds approximately to the deformation temperature for the plastic deformation of the pane of glass.

30. A method according to claim 22, wherein the sintering is effected at a temperature which corresponds approximately to the deformation temperature for the plastic deformation of the pane of glass.

31. A method according to claim 30, wherein the sintering is effected at a temperature of between about 500° C. and 700° C.

32. A method according to claim 31, wherein the sintering is at a temperature of about 600° C.

33. A method according to claim 21, wherein the resinate is applied to a flat pane of the glass and sintered on it with simultaneous deformation by a bending of the pane glass.

34. A method according to claim 33, wherein the deformation by bending is effected by gravitational bending.

35. A method according to claim 33, wherein the deformation by bending is effected by press bending in a press-bending furnace.

36. A method according to claim 33, wherein after the deformation by bending, there is a step of heating a region of the pane of glass bearing the resinate for a short time at a temperature which is above the deformation temperature for a plastic deformation of the pane of glass.

37. A method according to claim 36, wherein the second step of heating is accomplished at a temperature of more than 700° C.

38. A method according to claim 36, wherein the second step of heating is limited to a period of time of at most 30 seconds.

39. A method according to claim 15, further comprising a step of applying an intended pattern consisting of a sinterable resinate to a flexible sheet, the flexible sheet being vaporizable at a temperature corresponding approximately to a sintering temperature of the resinate.

40. A method according to claim 15, further comprising steps of:

applying an intended pattern of a sinterable resinate upon a support sheet;

applying a flexible foil layer upon a support sheet covering the intended resinate pattern; and wherein the adherence of the resinate pattern to the support sheet is less than to the foil layer, and the flexible foil layer is vaporizable at a temperature corresponding approximately to a sintering temperature of the resinate.

* * * * *